(12) United States Patent
Maurer et al.

(10) Patent No.: US 8,709,767 B2
(45) Date of Patent: Apr. 29, 2014

(54) PROCESS FOR THE ENZYMATIC REDUCTION OF ENOATES

(71) Applicants: Stephan Maurer, Neustadt-Gimmeldingen (DE); Bernhard Hauer, Fussgönheim (DE); Melanie Bonnekessel, Mannheim (DE); Kurt Faber, Graz (AT); Clemens Stückler, Graz (AT)

(72) Inventors: Stephan Maurer, Neustadt-Gimmeldingen (DE); Bernhard Hauer, Fussgönheim (DE); Melanie Bonnekessel, Mannheim (DE); Kurt Faber, Graz (AT); Clemens Stückler, Graz (AT)

(73) Assignee: BASF SE (DE)

( * ) Notice: Subject to any disclaimer, the term of this patent is extended or adjusted under 35 U.S.C. 154(b) by 0 days.

(21) Appl. No.: 13/658,328

(22) Filed: Oct. 23, 2012

(65) Prior Publication Data

US 2013/0045513 A1 Feb. 21, 2013

Related U.S. Application Data

(63) Continuation of application No. 13/375,979, filed as application No. PCT/EP2010/057511 on May 31, 2010, now abandoned.

(60) Provisional application No. 61/227,794, filed on Jul. 23, 2009.

(30) Foreign Application Priority Data

Jun. 4, 2009 (EP) .................................. 09161888
Jul. 17, 2009 (EP) .................................. 09165744

(51) Int. Cl.
*C12P 7/24* (2006.01)
*C12P 7/40* (2006.01)
*C12P 7/26* (2006.01)

(52) U.S. Cl.
USPC ........................... 435/147; 435/136; 435/148

(58) Field of Classification Search
None
See application file for complete search history.

(56) References Cited

U.S. PATENT DOCUMENTS

| | | | |
|---|---|---|---|
| 8,313,923 B2 * | 11/2012 | Sturmer et al. ............ | 435/61 |
| 2008/0293111 A1 | 11/2008 | Schaedler et al. | |
| 2010/0189777 A1 | 7/2010 | Schwaneberg et al. | |
| 2010/0273223 A1 | 10/2010 | Hauer et al. | |
| 2010/0291640 A1 | 11/2010 | Stuermer et al. | |
| 2010/0291641 A1 | 11/2010 | Dauwel et al. | |
| 2010/0304448 A1 | 12/2010 | Sturmer et al. | |
| 2010/0311037 A1 | 12/2010 | Hauer et al. | |
| 2011/0137002 A1 | 6/2011 | Hauer et al. | |
| 2011/0171700 A1 | 7/2011 | Breuer et al. | |

FOREIGN PATENT DOCUMENTS

| WO | WO 2008058951 A1 * | 5/2008 |
|---|---|---|
| WO | WO-2010139651 A2 | 12/2010 |
| WO | WO-2010139719 A2 | 12/2010 |
| WO | WO-2011012632 A2 | 2/2011 |
| WO | WO-2011032990 A1 | 3/2011 |
| WO | WO-2011033039 A1 | 3/2011 |
| WO | WO-2011036233 A1 | 3/2011 |
| WO | WO-2011051433 A2 | 5/2011 |
| WO | WO-2011064259 A1 | 6/2011 |
| WO | WO-2011092345 A1 | 8/2011 |

OTHER PUBLICATIONS

Mussig et al., "A novel stress-inducible 12-oxophytodienoate reductase from *Arabidopsis thaliana* provides a potential link between Brassinosteroid-action and Jasmonic-acid synthesis", J. Plant Physiol. 157:143-152, 2000.*
Stueckler et al., Tetrahedron 66:663-667, Nov. 2009.*
Swiderska, M., "Application of *Saccharomyces carlsbergensis* Old Yellow Enzyme in Synthesis of Chiral Ketones and Building Blocks for β-Amino Acids", Dissertation, University of Florida, 2007.*
Chaparro-Riggers et al., Adv. Synth. Catal. 349:1521-1531, 2007.*
van der Werf et al., Microbiology 146:1129-1141, 2000.*
Trytek et al., Biotechnol. Prog. 23:131-137, 2007.*
GenPept Accession No. Q02899, Nov. 2007, 8 pages.*
UniProtKB Accession No. P54550, Oct. 1996, 1 page.*
UniProtKB Accession No. EBP1_CANAX, May 2009, 2 pages.*

(Continued)

*Primary Examiner* — David J Steadman
(74) *Attorney, Agent, or Firm* — Novak Druce Connolly Bove + Quigg LLP

(57) ABSTRACT

A process for the enzymatic reduction of an enoate (1) wherein the C═C bond of the enoate (1) is stereoselectively hydrogenated in the presence of an enoate-reductase and an oxidizable co-substrate (2) in a system which is free of NAD (P)H,

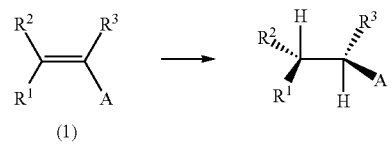

(1)

in which A is a ketone radical (—CRO), an aldehyde radical (—CHO), a carboxyl radical (—COOR), with R═H or optionally substituted $C_1$-$C_6$-alkyl radical, $R^1$, $R^2$ and $R^3$ are independently of one another H, —O—$C_1$-$C_6$-alkyl, —O—W with W=a hydroxyl protecting group, $C_1$-$C_6$-alkyl, which can be substituted, $C_2$-$C_6$-alkenyl, carboxyl, or an optionally substituted carbo- or heterocyclic, aromatic or nonaromatic radical, or one of $R^1$, $R^2$ and $R^3$ is a —OH radical, or $R^1$ is linked to $R^3$ so as to become part of a 4-8-membered cycle, or $R^1$ is linked to R so as to become part of a 4-8-membered cycle, with the proviso that $R^1$, $R^2$ and $R^3$ may not be identical.

4 Claims, 1 Drawing Sheet

(56) References Cited

OTHER PUBLICATIONS

Vaz A D N et al, Biochemistry, 1995, vol. 34, Issue 13, pp. 4246-4256 (Search report).
Buckman James et al, Biochemistry, 1998, vol. 37, Issue 40, pp. 14326-14336.
Karplus P Andrew et al, Faseb Journal, 1995, vol. 9, Issue 15, pp. 1518-1526 (Search Report).
Hall M et al, European Journal of Organic Chemistry, 2008, vol. 9, pp. 1511-1516.
Hall M et al, Advanced Synthesis & Caralysis Wiley-VCH, 2008, vol. 350, Issue 3, pp. 411-418.
Stuermer et al, Current Opinion in Chemical Biology, 2007, vol. 11, Issue 2, pp. 203-213.
Bisogno Fabricio R et al, The Journal of Organic Chem, 2009, vol. 74, Issue 4, pp. 1730-1732.
Sairo K et al, The Journal of Biological Chem, 1991, vol. 266, Issue 31, pp. 20720-20724 (Search Report).
Stott K et al, The Journal of Biological Chem, 1993, vol. 268, Issue 9, pp. 6097-6106 (Search Report).
R.N. Patel, "Biochatalysis in the pharmaceutigal and biotechnology industry", CRC Press, Boca Raton, 2007, pp. 623-644.
U. Kragl, D. Vasic-Racki, C. Wandrey, Indian J. Chem. Sect.B, 1993, vol. 32B, pp. 103-117.
J.M.Vritis, A.K.White, et al, Angew. Chem. Int., 2002, vol. 41, pp. 3391-3393.
T.W. Johannes, R.D. Woodyer, Biotechnol.Bioeng., 2006, vol. 96, pp. 18-26.
C.Breithaupt, J. Strassner, et al, Structure, 2001, vol. 9, pp. 419-429.
K.Kitzing, E.B. Fitzpatrick, et al, J.Biol. Chem., 2005, vol. 280, pp. 27904-27913.
A. Müller, B. Hauer, et al, Biotechnol. Bioeng, 2007, vol. 98, pp. 22-29.
T.Barna, H.L. Messiha et al, J. Biol. Chem., 2002, vol. 277, pp. 30976-30983.
H.L. Messiha, A.W. Munroe, et al, J. Biol. Chem., 2005, vol. 280, pp. 10695-10709.
R.E. Williams, D.A. Rathbone, et al, Appl. Environ. Microbiol., 2004, vol. 70, pp. 3566-3574.
A. Taglieber, F. Schulz, et al, ChemBioChem, 2008, vol. 9, pp. 565-572.
F. Hollmann, A. Taglieber, et al, Angew. Chem.Int. Ed., 2007, vol. 46, pp. 2903-2906.
C. Wandrey, Chem. Rec, 2004, vol. 4, pp. 254-265.
International Search Report for PCT/EP2010/0575116, Jan. 14, 2011.

* cited by examiner

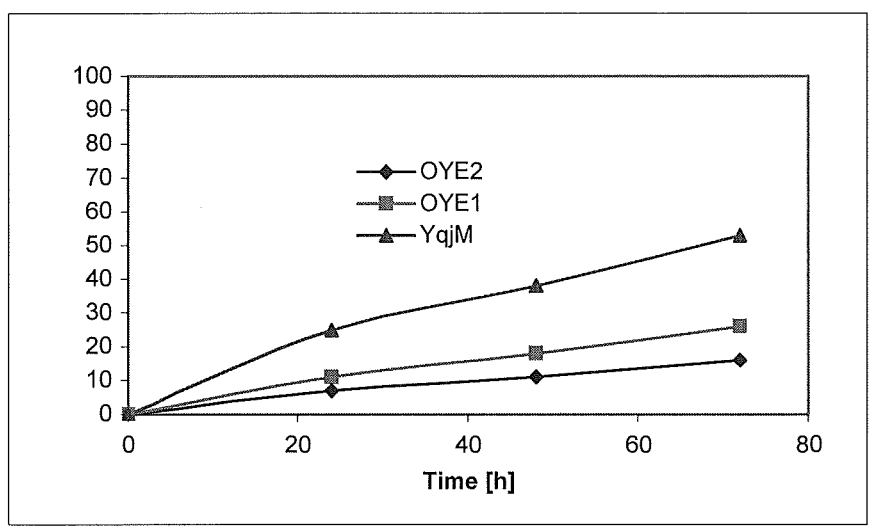

PROCESS FOR THE ENZYMATIC REDUCTION OF ENOATES

CROSS REFERENCE TO RELATED APPLICATIONS

This application is a continuation application of U.S. patent application Ser. No. 13/375,979, filed Dec. 2, 2011, which is a national stage application (under 35 U.S.C. §371) of PCT/EP2010/057511filed May 31, 2010, which claims priority to U.S. Provisional Application 61/227,794filed on Jul. 23, 2009, to European Application 09165744.5 filed Jul. 17, 2009, and to European Application 09161888.4 filed on Jun. 4, 2009, the entire contents of all of which are incorporated herein by reference.

The present invention relates to a novel process for the enzymatic reduction of enoates.

The disproportionation of conjugated enones, such as cyclohex-2-enone, has been described as minor catalytic activity for several flavoproteins exhibiting enoate reductase-activity. In the context of these studies, this phenomenon has been generally considered as a side reaction, rather than as a useful transformation. Overall, this reaction constitutes a flavin-dependent hydrogen-transfer, during which an equivalent of [2H] is formally transferred from one enone molecule (being oxidised) onto another one (being reduced). In case of cyclohex-2-enone, this leads to the formation of an equimolar amount of cyclohexanone and cyclohex-2,5-dien-one. The latter spontaneously tautomerises to form phenol, going in hand with the generation of an aromatic system, which provides a large driving force (within a range of 30 kcal/M) for the reaction.

BRIEF DESCRIPTION OF THE DRAWING

FIG. 1 shows the time course of reduction of 1 using 2 as hydrogen-donor (cf. scheme p. 8).

DETAILED DESCRIPTION OF THE INVENTION

The invention relates to a process for the enzymatic reduction of an enoate (1) wherein the C=C bond of the enoate (1) is stereoselectively hydrogenated in the presense of an enoat-reductase and an oxidizable co-substrate (2) in a system which is free of NAD(P)H,

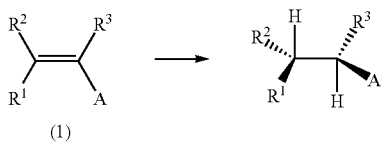

(1)

in which
A is a ketone radical (—CRO), an aldehyde radical (—CHO), a carboxyl radical (—COOR), with R=H or optionally substituted $C_1$-$C_6$-alkyl radical,
$R^1$, $R^2$ and $R^3$ are independently of one another H, —O—$C_1$-$C_6$-alkyl, —O—W, with W=a hydroxyl protecting group, $C_1$-$C_6$-alkyl which can be substituted, $C_2$-$C_6$-alkenyl, carboxyl, or an optionally substituted carbo- or heterocyclic, aromatic or nonaromatic radical, or $R^1$ is linked to $R^3$ so as to become part of a 4-8-membered cycle, or $R^1$ is linked to R so as to become part of a 4-8-membered cycle, with the proviso that $R^1$, $R^2$ and $R^3$ may not be identical. Preferably, the C=C bond of the enoate (1) is enantioselectively or diastereoselectively hydrogenated.

One of the rests $R^1$, $R^2$ and $R^3$ may also be a —OH group; however in this case the formula (1) depicts the enol form which is in equilibrium with its keto form (formula 1a), i.e. $R^1$=formyl (see above):

For $R^1$=OH the equilibrium is:

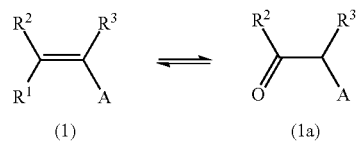

(1)          (1a)

A system which is free of NAD(P)H means that no external $NAD^+$, and/or NADH and/or $NADP^+$ and/or NADPH is added to the system.

Preferred co-substrates (2) are enoates having a chemical structure which has been described for the enoates (1) above. In a much preferred embodiment the cosubstrate (2) has the identical chemical structure as the enoate (1) used for the specific reaction. In another preferred embodiment the cosubstrate (2) has not the identical chemical structure as the enoate (1) used for the specific reaction.

Another embodiment of the invention uses cosubstrates (2) which after having been oxidized during the reaction possess a conjugated, preferably an aromatic, electronic system.

Unless stated otherwise,
—O—$C_1$-$C_6$-alkyl means in particular —O-methyl, —O-ethyl, —O-propyl, —O-butyl, —O-pentyl or —O-hexyl and the corresponding singly or multiply branched analogs such as —O-isopropyl, —O-isobutyl, —O-sec-butyl, —O-tert-butyl, —O-isopentyl or —O-neopentyl; with preference being given in particular to the —O—$C_1$-$C_4$-alkyl radicals;
—O—W means a hydroxyl protecting group W which is bound to oxygen in particular such as —O-allyl, —O-benzyl, O-tetrahydropyranyl, —O-tert. Butyldimethylsilyl (TBDMS), —O-tert. Butyldiphenylsilyl (TBDPS)
$C_1$-$C_6$-alkyl means in particular methyl, ethyl, propyl, butyl, pentyl or hexyl and the corresponding singly or multiply branched analogs such as isopropyl, isobutyl, sec-butyl, tert-butyl, isopentyl or neopentyl; with preference being given in particular to the $C_1$-$C_4$-alkyl radicals;
$C_1$-$C_6$-alkyl which can be substituted means in particular methyl, ethyl, propyl, butyl, pentyl or hexyl and the corresponding singly or multiply branched analogs such as isopropyl, isobutyl, sec-butyl, tert-butyl, isopentyl or neopentyl; where 1, 2 oder 3 hydrogen atoms can be substituted by a group selected from F, Cl, Br, J, OH, O—W, SH, NH2. Preferred are single-substituted $C_1$-$C_6$-alkyls with preference being given in particular to $CH_2OH$ and to $CH_2$ O—W.
$C_2$-$C_6$-alkenyl means in particular the monounsaturated analogs of the above-mentioned alkyl radicals having from 2 to 6 carbon atoms, with preference being given in particular to the corresponding $C_2$-$C_4$-alkenyl radicals,
carboxyl means in particular the group COOH,
carbo- and heterocyclic aromatic or nonaromatic rings mean in particular optionally fused rings having from 3 to 12 carbon atoms and if appropriate from 1 to 4 heteroatoms such as N, S and O, in particular N or O. Examples which may be mentioned are cyclopropyl, cyclobutyl, cyclopentyl, cyclohexyl, cycloheptyl, the mono- or polyunsaturated analogs thereof such as cyclobutenyl, cyclopentenyl, cyclohexenyl, cycloheptenyl, cyclohexadienyl, cycloheptadienyl; phenyl and naphthyl; and 5- to 7-membered saturated or unsaturated heterocyclic radicals having from 1 to 4 heteroatoms which are selected from O, N and S, where the heterocycle may optionally be fused to a further heterocycle or carbocycle. Mention should be made in particular of heterocyclic radicals derived from pyrrolidine, tetrahydrofuran, piperidine, morpholine, pyrrole, furan, thiophene, pyrazole, imidazole, oxazole, thiazole, pyridine, pyran, pyrimidine, pyridazine, pyrazine, coumarone, indole and quinoline. The cyclic radicals, but also the abovementioned —O-alkyl, alkyl and alkenyl radicals, may optionally be substituted one or more times, such as, for example, 1, 2 or 3 times. Mention should be made as examples of suitable substituents of: halogen, in particular F, Cl, Br; —OH, —SH, —NO$_2$, —NH$_3$, —SO$_3$H, C$_1$-C$_4$-alkyl and C$_2$-C$_4$-alkenyl, C$_1$-C$_4$-alkoxy; and hydroxy-C$_1$-C$_4$-alkyl; where the alkyl and alkenyl radicals are as defined above, and the alkoxy radicals are derived from the above-defined corresponding alkyl radicals.

The radicals R$^1$ and R$^3$ may also be linked directly to one another so as to form together with the double bond to be reduced a 4-8-, preferably a 5- or 6-membered cycle, for example a cyclopentene or cyclohexene structure which may also be optionally substituted, for example by alkyl, preferably methyl radicals.

The radicals R$^1$ and R may also be linked directly to one another so as to form together with the double bond to be reduced a 4-8-, preferably a 5- or 6-membered cycle, for example a cyclopentene or cyclohexene structure which may also be optionally substituted, for example by —O-alkyl or alkyl, preferably methoxy or methyl radicals.

The abovementioned 4-8-membered cycles may be both carbocycles, i.e. only carbon atoms form the cycle, and heterocycles, i.e. heteroatoms such as O; S; N, are present in the cycle. If desired, these carbo- or heterocycles may also still be substituted, i.e. hydrogen atoms are replaced with heteroatoms. For example, N-phenylsuccinimides (see substrate 3 below) are to be considered such substituted heterocycles which are the result of R$^1$ and R forming a cycle.

Particularly advantageous embodiments of the invention comprise the enzymatic conversion of the following enoates (1) (substrates) to the corresponding hydrogenated compounds:

Substrate 1

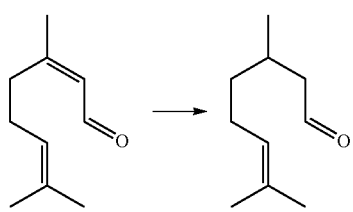

Substrate 2

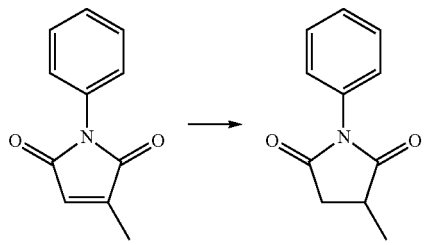

Substrate 3

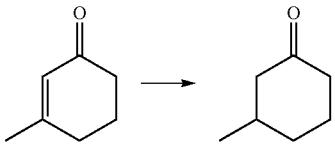

Substrate 4

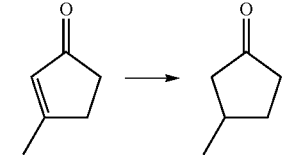

Substrate 5

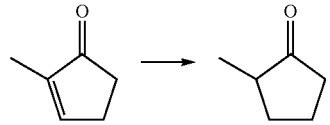

Substrate 6

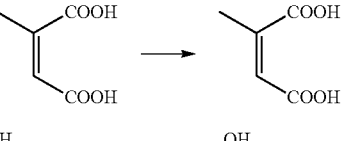

Substrate 7

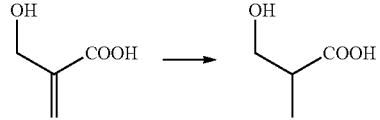

Preferred Enoate-Reductases (1):

In addition, the reductases suitable for the method of the invention (which are occasionally also referred to as enoate reductases) have a polypeptide sequence as shown in SEQ ID NO:1, 2, 3, 4 or a polypeptide sequence which has at least 80% such as, for example, at least 90%, or at least 95% and in particular at least 97%, 98% or 99% sequence identity with SEQ ID NO: 1, 2, 3, 4.

A polypeptide having SEQ ID NO:1 is known under the name OYE1 from *Saccharomyces carlsbergensis* (Genbank Q02899).

A polypeptide having SEQ ID NO:2 is encoded by the OYE2 gene from baker's yeast (*Saccharomyces cerevisiae* gene locus YHR179W) (Genbank Q03558).

A polypeptide having SEQ ID NO:3 is encoded by the YqjM gene from *Bacillus subtilis*.

A polypeptide having SEQ ID NO:4 is encoded by the FCC248 gene from estrogen binding protein.

The sequence identity is to be ascertained for the purposes described herein by the "GAP" computer program of the Genetics Computer Group (GCG) of the University of Wisconsin, and the version 10.3 using the standard parameters recommended by GCG is to be employed.

Such reductases can be obtained starting from SEQ ID NO: 1, 2, 3, 4 by targeted or randomized mutagenesis methods known to the skilled worker. An alternative possibility is, however, also to search in microorganisms, preferably in those of the genera *Alishewanella, Alterococcus, Aquamonas, Aranicola, Arsenophonus, Azotivirga, Brenneria, Buchnera* (*aphid Pendosymbionts*), *Budvicia, Butkauxella, Candidatus Phlomobacter, Cedecea, Citrobacter, Dickeya, Edwardsiella, Enterobacter, Erwinia, Escherichia, Ewingella, Grimontella, Hafnia, Klebsiella, Kluyvera, Leclercia, Leminorella, Moellerella, Morganella, Obesumbacterium, Pantoea, Pectobacterium, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhabdus, Yersinia* or *Yokenella*, for reductases which catalyze the abovementioned model reaction and whose amino acid sequence already has the required sequence identity to SEQ ID NO: 1, 2, 3, 4 is obtained by mutagenesis methods.

The reductase can be used in purified or partly purified form or else in the form of the microorganism itself. Methods for obtaining and purifying dehydrogenases from microorganisms are well known to the skilled worker.

The reaction can be carried out in aqueous or nonaqueous reaction media or in 2-phase systems or (micro)emulsions. The aqueous reaction media are preferably buffered solutions which ordinarily have a pH of from 4 to 8, preferably from 5 to 8. The aqueous solvent may, besides water, additionally comprise at least one alcohol, e.g. ethanol or isopropanol, or dimethyl sulfoxide.

Nonaqueous reaction media mean reaction media which comprise less than 1% by weight, preferably less than 0.5% by weight, of water based on the total weight of the liquid reaction medium. The reaction can in particular be carried out in an organic solvent.

Suitable organic solvents are for example aliphatic hydrocarbons, preferably having 5 to 8 carbon atoms, such as pentane, cyclopentane, hexane, cyclohexane, heptane, octane or cyclooctane, halogenated aliphatic hydrocarbons, preferably having one or two carbon atoms, such as dichloromethane, chloroform, tetrachloromethane, dichloroethane or tetrachloroethane, aromatic hydrocarbons such as benzene, toluene, the xylenes, chlorobenzene or dichlorobenzene, aliphatic acyclic and cyclic ethers or alcohols, preferably having 4 to 8 carbon atoms, such as ethanol, isopropanol, diethyl ether, methyl tert-butyl ether, ethyl tert-butyl ether, dipropyl ether, diisopropyl ether, dibutyl ether, tetrahydrofuran or esters such as ethyl acetate or n-butyl acetate or ketones such as methyl isobutyl ketone or dioxane or mixtures thereof. The aforementioned ethers, especially tetrahydrofuran, are particularly preferably used.

The reduction with reductase can for example be carried out in an aqueous organic reaction medium such as, for example, water/isopropanol in any mixing ratio such as, for example, 1:99 to 99:1 or 10:90 to 90:10, or an aqueous reaction medium.

The substrate (1) is preferably employed in the enzymatic reduction in a concentration from 0.1 g/l to 500 g/l, particularly preferably from 1 g/l to 50 g/l, and can be fed in continuously or discontinuously.

The enzymatic reduction ordinarily takes place at a reaction temperature below the deactivation temperature of the reductase employed and above −10° C. It is particularly preferably in the range from 0 to 100° C., in particular from 15 to 60° C. and specifically from 20 to 40° C., e.g. at about 30° C.

A possible procedure for example is to mix the substrate (1) with the reductase and if appropriate the solvent thoroughly, e.g. by stirring or shaking. However, it is also possible to immobilize the reductase in a reactor, for example in a column, and to pass a mixture comprising the substrate through the reactor. For this purpose it is possible to circulate the mixture through the reactor until the desired conversion is reached.

During this reaction, the flavin-cofactor is recycled internally and no external cofactor, such as NADH or NADPH, which are commonly used to recycle reduced flavoproteins are required. In these classic nicotinamide-dependent systems, C=C-bonds are reduced at the expense of an external hydride donor, such as formate, glucose, glucose-6-phosphate or phosphite, which requires a second (dehydrogenase) enzyme, such as FDH, GDH, G-6-PDH [i] or phosphite-DH [ii], respectively. This technology is generally denoted as 'coupled-enzyme-approach' and depends on the concurrent operation of two independent redox enzymes for substrate-reduction and co-substrate-oxidation, resp.

In order to avoid the use of a second nicotinamide-dependent redox enzyme, the disproportionation of enones can be envisaged to function via a more simple system, denoted as 'coupled-substrate-approach', which solely depends on a single flavoprotein. Thereby, the use of (i) an additional redox-enzyme and (ii) an additional redox-cofactor, such as NAD(P)H, can be omitted.

EXPERIMENTAL SECTION

During an initial screening, a set of cloned and overexpressed enoate reductases was tested for their catalytic activity in the disproportionation of cyclohex-2-enone. To our delight, the desired disproportionation activity was observed in a variey of OYE homologs, most prominent in YqjM, OYE1, OYE2 and estrogen-binding protein.

Example 1

General Procedure for the Screening for Enzymatic Disproportionation of cyclohex-2-enone An aliquot of the isolated enzyme OPR1, OPR3, YqjM, OYE1, OYE2, OYE3, *Zymonas mobilis* ER, NEM-Red, MOR-Red and PETN-Red (protein purity>90%, protein content 90-110 µg/mL) was added to a TriHCl buffer solution (0.8 mL, 50 mM, pH 7.5) containing cyclohex-2-enone (10 mM). The mixture was shaken at 30° C. and 120 rpm for 24 h and the products were extracted with EtOAc (2×0.5 mL). The combined organic phases were dried ($Na_2SO_4$) and the resulting samples were analyzed on achiral GC. Products were identified by comparison with authentic reference materials via co-injection on GC-MS and achiral GC. Column: 6% Cyanopropyl-phenyl phase capillary column (Varian CP-1301, 30 m, 0.25 mm, 0.25 µm), detector temperature 250° C., split ratio 30:1; temperature program: 80° C.; hold 2 min.; rise to 120° C. with 5° C./min. Retention times: cyclohex-2-enone 2.97 min, cyclohexanone 2.43 min, phenol 4.98 min.

| Enzyme [a] | Conv. [%] |
|---|---|
| OPR1 | <1 |
| OPR3 | <1 |

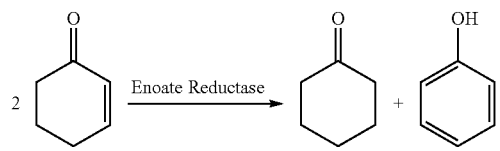

| Enzyme[a] | Conv. [%] |
|---|---|
| YqjM | 85 |
| OYE1 | 92 |
| OYE2 | 75 |
| OYE3 | 7 |
| Zym-mob ER | 7 |
| NEM-Red | <1 |
| MOR-Red | <1 |
| PETN-Red | 0 |
| FCC248[b] | 45 |
| FCC249[c] | 13 |

[a] OPR1, OPR3 = oxophytodienoate reductase isoenzymes 1 and 3, resp., from tomato [iii]; YqjM = OYE-homolog from *Bacillus subtilis* [iv]; OYE1-3 = OYEs from yeasts [v]; Zym-mob ER = *Zymomonas mobilis* enoate reductase [vi]; MOR-Red = morphinone reductase [vii]; NEM-Red = N-ethylmaleimide reductase; PETN-Red = pentaerythritol tetranitrate reductase [viii];

[b] FCC249 = *E. coli* expressing native estrogen-binding protein [ix];

[c] FCC248 = *E. coli* expressing synthetic estrogen-binding protein, both preparations were employed as crude cell-free extract [x].

Taking these relative activities as a lead, further experiments were performed using the three 'champions', YqjM, OYE1 and OYE2.

In order to turn the scrambling-like non-directed hydrogen-transfer reaction occurring between two identical cyclohexenone molecules into a useful directed redox process, where one substrate is dehydrogenated/oxidised, while another is hydrogenated/reduced, two suitable enone substrates—one only being oxidised, the other only being reduced—have to be coupled. During our previous studies on NAD(P)H-coupled enone reduction, we observed that alpha-substituted cyclic enones were quickly reduced, whereas alkyl-substituents in the beta-position severely impeded the reaction rate. Hence, we envisaged to couple an alpha- and a beta-substituted enone as substrates, being reduced and oxidised, resp.

In order to check the feasibility of this protocol, we investigated the disproportionation of 2-(1) and 3-methylcyclohex-2-enone (2); under identical conditions as for cyclohex-2-enone. With all

| | 1a [%] | | 1b [%] | | 2a [%] | | 2b [%] | |
|---|---|---|---|---|---|---|---|---|
| Enzyme | 24 h | 72 h | 24 h | 72 h | 24 h | 72 h | 24 h | 72 h |
| OYE1 | 10 | 12 | 6 | 9 | 4 | 9 | 6 | 14 |
| OYE2 | 7 | 9 | 3 | 7 | 2 | 4 | 3 | 8 |
| YqjM | 7 | 7 | 3 | 5 | 0 | 0 | 18 | 30 | of the enzymes tested, the relative rate of disproportionation for 1 was higher than those for 2, meaning that the C=C-bond of alpha-methylcyclohex-2-enone was faster reduced than its beta-substituted analog 2. This difference was most pronounced for YqjM.

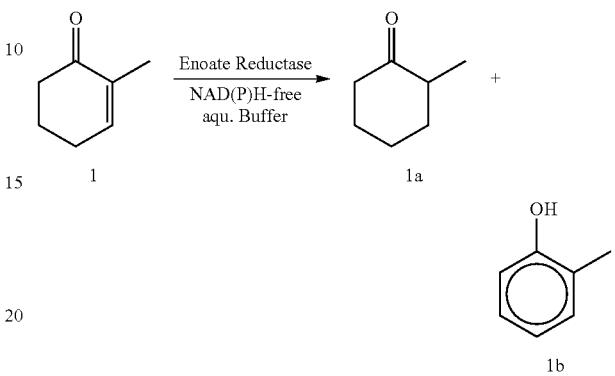

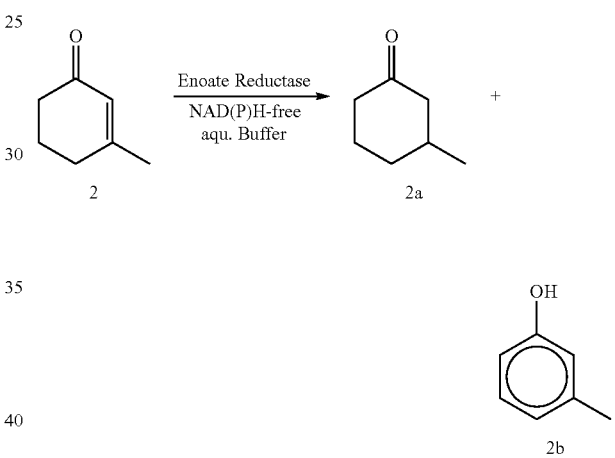

Encouraged by these results, we next attempted the coupled-substrate hydrogen-transfer between 2-(1) and 3-methylcyclohex-2-enone (2) as substrates to be reduced and oxidised, resp., in a directed fashion.

The results of these experiments provided a clear proof-of-principle:

(i) Depending on the enzyme, the desired reduced alpha-methyl derivative 1a was formed in up to 38% conversion, the oxidised beta-methyl analog 2b was detected in roughly equimolar amounts.

(ii) In contrast, only trace amounts of the corresponding cross-hydrogen-transfer products, which would be expected from undesired oxidation of 1 and reduction of 2 were found, indicating that the mono-directional hydrogen-transfer indeed worked as envisaged.

(iii) Investigation of the optical purity and absolute configuration of 1a revealed that the product was formed in the same selective fashion as in the classic reduction-mode using NAD(P)H-recycling, ensuring that the chiral induction process of the enzymes was unchanged [xi].

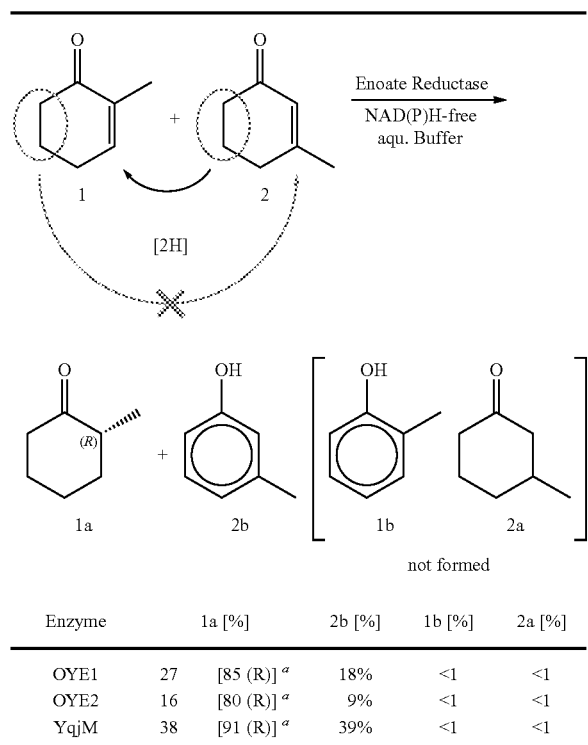

| Enzyme | 1a [%] | 2b [%] | 1b [%] | 2a [%] |
|---|---|---|---|---|
| OYE1 | 27 | [85 (R)][a] | 18% | <1 | <1 |
| OYE2 | 16 | [80 (R)][a] | 9% | <1 | <1 |
| YqjM | 38 | [91 (R)][a] | 39% | <1 | <1 |

[a] Enantiomeric excess [%] and absolute configuration.

Coupled-substrate C=C-bond reduction of 2-methylcyclohex-2-enone (1) using 3-methylcyclohex-2-enone (2) as hydrogen donor.

An aliquot of the isolated enzyme YqjM, OYE1, OYE2, (protein purity >90%, protein content 90-110 μg/mL) was added to a Tris-HCl buffer solution (0.8 mL, 50 mM, pH 7.5) containing the substrate 1 (110 mM) and the co-substrate 2 (10 mM). The mixture was shaken at 30° C. and 120 rpm for 24 h and products were extracted with EtOAc (2×0.5 mL). The combined organic phases were dried ($Na_2SO_4$) and the resulting samples were analyzed on achiral GC. Products were identified by comparison with authentic reference materials via co-injection on GC-MS and achiral GC. Column: 14% cyanopropyl-phenyl phase capillary column (J&W Scientific DB-1701, 30 m, 0.25 mm, 0.25 μm), detector temperature 250° C., split ratio 30:1. Temperature program: 110° C., hold 5 min, rise to 200° C. with 10° C./min, hold 2 min. 2-Methylcyclohexenone (1) 4.38 min; 2-methylcyclohexanone (1a): 3.70 min; 3-methylcyclohexenone (2) 6.27 min; 3-methylphenol (2b) 7.90 min; 2-methylphenol (1b) 7.02 min; 3-methylcyclohexanone (2a) 3.63 min.

In order to drive the reduction of 1 further towards completion, increasing amounts of co-substrate 2 were employed (cf. scheme above). As can be deduced from the amounts of reduction product 1a formed, elevated co-substrate concentrations had little effect, which is presumably due to enzyme inhibition caused by elevated cosubstrate concentrations. This phenomenon is also common for the asymmetric bioreduction of carbonyl compounds catalysed by alcohol dehydrogenases using the coupled-substrate method.

|  | Ratio of 1:2 | | |
|---|---|---|---|
| Enzyme | 1:1 | 1:1.5 | 1:2 |
| OYE1 | 12 | 11 | 10 |
| OYE2 | 8 | 7 | 5 |
| YqjM | 26 | 27 | 27 |

In oder to verify this hypothesis, the reaction was performed with a 1:1 ratio of 1 and 2 using increasing amounts of enzyme, added at intervals of 24 h. In this case, the conversion could be significantly improved, which underscores the above mentioned co-substrate inhibition.

|  | Enzyme portion[a] | | |
|---|---|---|---|
| Enzyme | 1 | 2 | 3 |
| OYE1 | 11% | 19% | 27% |
| OYE2 | 6% | 13% | 19% |
| YqjM | 24% | 48% | 65% |

[a] Amounts of reduction product 1a formed by addition of equal amounts of enzyme (100 mL each) at intervals of 24 h.

Monitoring the reaction over time showed that the process was mainly limited by the catalytic power of the enzyme employed. The conversion steadily increased, indicating that the enzyme remained catalytically active up to 72 h, which proved that the inhibition was largely reversible (FIG. 1).

FIG. 1 shows the time course of reduction of 1 using 2 as hydrogen-donor (cf. scheme p. 8).

Aiming to extend the applicability of this nicotinamide-free C=C-bond reduction system, we subjected two further substrates (3, 4), which are known to be reduced by enoate reductases in combination with NAD(P)H-recycling, to the hydrogen-transfer protocol in presence of equimolar amounts of beta-methylcyclohex-2-enone (2) as hydrogen donor. In both cases, the reduction proceeded smoothly and furnished the corresponding (R)-configured products 3a and 4a in the same enantiomeric composition as in the nicotinamide-driven process. Among the enzymes tested, YqjM was clearly best.

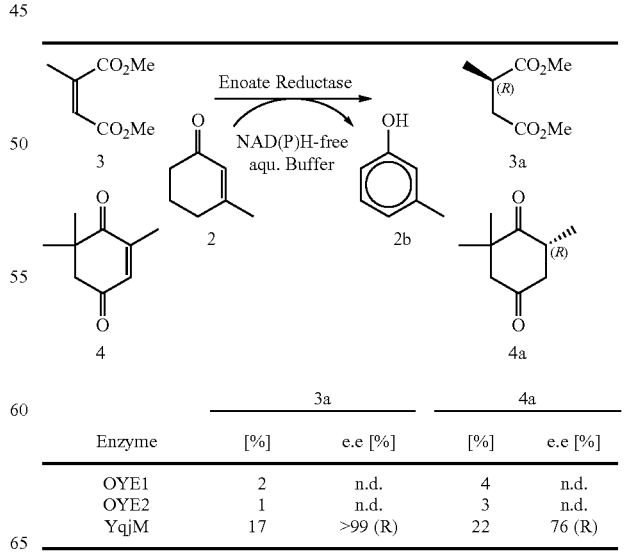

|  | 3a | | 4a | |
|---|---|---|---|---|
| Enzyme | [%] | e.e [%] | [%] | e.e [%] |
| OYE1 | 2 | n.d. | 4 | n.d. |
| OYE2 | 1 | n.d. | 3 | n.d. |
| YqjM | 17 | >99 (R) | 22 | 76 (R) | n.d. = not determined.

Since the use of equimolar amounts of 3-methylcyclohex-2-enone (2) as co-substrate would be economically desastrous, a cheaper alternative for a hydrogen donor was sought. After attempts using 1-indanone and hydroquinone failed, cyclohexane-1,4-dione (5)—yielding 1,4-dihydroxybenzene (hydroquinone, 5a)—as oxidation product was found to provide a suitable alternative. Substrate 3 showed even enhanced conversion as compared to beta-methylcyclohex-2-enone (2) as co-substrate.

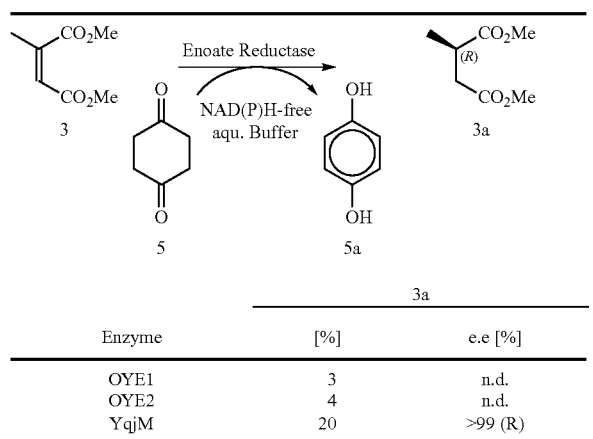

| Enzyme | 3a [%] | e.e [%] |
|---|---|---|
| OYE1 | 3 | n.d. |
| OYE2 | 4 | n.d. |
| YqjM | 20 | >99 (R) | n.d. = not determined.

Upon closer examination using YqjM, this reaction showed similar effects of reversible co-substrate inhibition, as indicated by the data below. In line with previous observations using 2 as hydrogen donor, the conversion gradually increased from 0 to 25% over a period of 7 days.

| | Conditions | | | | | |
|---|---|---|---|---|---|---|
| | Ratio of 3:5 | | | Enzyme amount[a] | | |
| | 1:1 | 1:1.5 | 1:2 | 1 x | 2 x | 3 x |
| 3a [%] | 17 | 20 | 20 | 12 | 20 | 25 |

[a]Equal amounts of enzyme (100 mL each) were added at intervals of 24 h.

Although the overall performance of this novel substrate-coupled C=C-bond reduction system has not yet reached the standard of nicotinamide-driven reactions, it has the following advantages compared to the following existing technologies:

(i) it depends only on a single flavoprotein and neither requires a second (dehydrogenase) recycling enzyme, nor a nicotinamide cofactor, and (ii) it has clear advantages to competitive alternative systems, such as the light-driven FAD-recycling [xii] and the electrochemical reduction via a (transition)metal-dependent mediator i. H. Yamamoto, A. Matsuyama, in: Biocatalysis in the pharmaceutical and biotechnology industry; R. N. Patel, ed., CRC Press, Boca Raton, 2007, pp. 623-44; C. Wandrey, Chem. Rec. 2004, 4, 254-65; U. Kragl, D. Vasic-Racki, C. Wandrey, Indian J. Chem., Sect. B 1993, 32B, 103-117.

ii. J. M. Vrtis, A. K. White, W. W. Metcalf, W. A. van der Donk, Angew. Chem. Int. Ed. 2002, 41, 3391-3; T. W. Johannes, R. D. Woodyer, H. Zhao, Biotechnol. Bioeng. 2006, 96, 18-26.

iii. C. Breithaupt, J. Strassner, U. Breitinger, R. Huber, P. Macheroux, A. Schaller, T. Clausen, Structure 2001, 9, 419-29.

iv. K. Kitzing, T. B. Fitzpatrick, C. Wilken, J. Sawa, G. P. Bourenkov, P. Macheroux, T. Clausen, J. Biol. Chem. 2005, 280, 27904-13.

v. M. Hall, C. Stueckler, B. hauer, R. Stuermer, T. Friedrich, M. Breuer, W. Kroutil, K. Faber, Eur. J. Org. Chem. 2008, 1511-6.

vi. A. Müller, B. Hauer, B. Rosche, Biotechnol. Bioeng. 2007, 98, 22-9.

vii. T. Barna, H. L. Messiha, C. Petosa, N. C. Bruce, N. S. Scrutton, P. C. E. Moody, J. Biol. Chem. 2002, 277, 30976-83; H. L. Messiha, A. W. Munroe, N. C. Bruce, I. Barsukov, N. S. Scrutton, J. Biol. Chem. 2005, 280, 10695-709.

viii. R. E. Williams, D. A. Rathbone, N. S. Scrutton, N. C. Bruce, Appl. Environ. Microbiol. 2004, 70, 3566-74.

ix. J. Buckman, S. M. Miller, Biochemistry 1998, 37, 14326-36.

x. Estrogen binding protein was cloned into E. coli by Nina Baudendistel at BASF AG.

xi. M. Hall, C. Stueckler, H. Ehammer, E. Pointner, G. Oberdorfer, K. Gruber, B. Hauer, R. Stuermer, P. Macheroux, W. Kroutil, K. Faber, Adv. Synth. Catal. 2008, 350, 411-8; M. Hall, C. Stueckler, B. Hauer, R. Stuermer, T. Friedrich, M. Breuer, W. Kroutil, K. Faber, Eur. J. Org. Chem. 2008, 1511-6.

xii. A. Taglieber, F. Schulz, F. Hollmann, M. Rusek, M. T. Reetz, Chem Bio Chem 2008, 9, 565-72; F. Hollmann, A. Taglieber, F. Schulz, M. T. Reetz, Angew. Chem. Int. Ed. 2007, 46, 2903-2906.

The invention claimed is:

1. A process for the enzymatic reduction of a compound (1), wherein the C=C bond of the compound (1) according to formula (1) is stereoselectively hydrogenated in the presence of an enoate-reductase and an oxidizable co-substrate which is a compound having a chemical structure according to formula (1) in a system which is free of NAD(P)H,

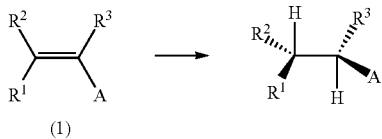

in which

A is a ketone radical (—CRO), an aldehyde radical (—CHO), a carboxyl radical (—COOR), with R =H or optionally substituted $C_1$-$C_6$-alkyl radical, $R^1$, $R^2$ and $R^3$ are independently of one another H, —O—$C_1$-$C_6$-alkyl, $C_1$-$C_6$-alkyl, which can be substituted, $C_2$-$C_6$-alkenyl, carboxyl, or an optionally substituted carbo- or heterocyclic, aromatic or nonaromatic radical, or $R^1$ is linked to $R^3$ so as to become part of a 4-8-membered cycle, or $R^1$ is linked to R so as to become part of a 4-8-membered cycle, with the proviso that $R^1$, $R^2$ and $R^3$ may not be identical; wherein the enoate reductase is selected from:
(i) an enoate reductase comprising at least one of the polypeptide sequences SEQ ID NO: 3 or 4; or
(ii) an enoate reductase comprising a polypeptide sequence which has at least 95% sequence identity with SEQ ID NO: 3.

2. The process according to claim 1, wherein the co-substrate is identical with the compound (1).

3. The process according to claim 1, wherein a molar ratio of compound (1) to co-substrate is from 1:1 to 1:3.

4. The process according to claim 1, wherein the C=C bond of the compound (1) is enantioselectively or diastereoselectively hydrogenated.

* * * * *

SEQUENCE LISTING

<160> NUMBER OF SEQ ID NOS: 4

<210> SEQ ID NO 1
<211> LENGTH: 399
<212> TYPE: PRT
<213> ORGANISM: saccharomyces carlsbergensis

<400> SEQUENCE: 1

Ser Phe Val Lys Asp Phe Lys Pro Gln Ala Leu Gly Asp Thr Asn Leu
1               5                   10                  15

Phe Lys Pro Ile Lys Ile Gly Asn Asn Glu Leu Leu His Arg Ala Val
            20                  25                  30

```
Ile Pro Pro Leu Thr Arg Met Arg Ala Leu His Pro Gly Asn Ile Pro
            35                  40                  45

Asn Arg Asp Trp Ala Val Glu Tyr Tyr Thr Gln Arg Ala Gln Arg Pro
    50                  55                  60

Gly Thr Met Ile Ile Thr Glu Gly Ala Phe Ile Ser Pro Gln Ala Gly
65                  70                  75                  80

Gly Tyr Asp Asn Ala Pro Gly Val Trp Ser Glu Glu Gln Met Val Glu
                85                  90                  95

Trp Thr Lys Ile Phe Asn Ala Ile His Glu Lys Lys Ser Phe Val Trp
                100                 105                 110

Val Gln Leu Trp Val Leu Gly Trp Ala Ala Phe Pro Asp Asn Leu Ala
            115                 120                 125

Arg Asp Gly Leu Arg Tyr Asp Ser Ala Ser Asp Asn Val Phe Met Asp
            130                 135                 140

Ala Glu Gln Glu Ala Lys Ala Lys Lys Ala Asn Asn Pro Gln His Ser
145                 150                 155                 160

Leu Thr Lys Asp Glu Ile Lys Gln Tyr Ile Lys Glu Tyr Val Gln Ala
                165                 170                 175

Ala Lys Asn Ser Ile Ala Ala Gly Ala Asp Gly Val Glu Ile His Ser
            180                 185                 190

Ala Asn Gly Tyr Leu Leu Asn Gln Phe Leu Asp Pro His Ser Asn Thr
            195                 200                 205

Arg Thr Asp Glu Tyr Gly Gly Ser Ile Glu Asn Arg Ala Arg Phe Thr
210                 215                 220

Leu Glu Val Val Asp Ala Leu Val Glu Ala Ile Gly His Glu Lys Val
225                 230                 235                 240

Gly Leu Arg Leu Ser Pro Tyr Gly Val Phe Asn Ser Met Ser Gly Gly
                245                 250                 255

Ala Glu Thr Gly Ile Val Ala Gln Tyr Ala Tyr Val Ala Gly Glu Leu
            260                 265                 270

Glu Lys Arg Ala Lys Ala Gly Lys Arg Leu Ala Phe Val His Leu Val
            275                 280                 285

Glu Pro Arg Val Thr Asn Pro Phe Leu Thr Glu Gly Glu Gly Glu Tyr
            290                 295                 300

Glu Gly Gly Ser Asn Asp Phe Val Tyr Ser Ile Trp Lys Gly Pro Val
305                 310                 315                 320

Ile Arg Ala Gly Asn Phe Ala Leu His Pro Glu Val Val Arg Glu Glu
                325                 330                 335

Val Lys Asp Lys Arg Thr Leu Ile Gly Tyr Gly Arg Phe Phe Ile Ser
            340                 345                 350

Asn Pro Asp Leu Val Asp Arg Leu Glu Lys Gly Leu Pro Leu Asn Lys
            355                 360                 365

Tyr Asp Arg Asp Thr Phe Tyr Gln Met Ser Ala His Gly Tyr Ile Asp
            370                 375                 380

Tyr Pro Thr Tyr Glu Glu Ala Leu Lys Leu Gly Trp Asp Lys Lys
385                 390                 395

<210> SEQ ID NO 2
<211> LENGTH: 399
<212> TYPE: PRT
<213> ORGANISM: Saccharomyces cerevisiae

<400> SEQUENCE: 2

Pro Phe Val Lys Asp Phe Lys Pro Gln Ala Leu Gly Asp Thr Asn Leu
1               5                   10                  15
```

-continued

Phe Lys Pro Ile Lys Ile Gly Asn Asn Glu Leu Leu His Arg Ala Val
         20                  25                  30

Ile Pro Pro Leu Thr Arg Met Arg Ala Gln His Pro Gly Asn Ile Pro
             35                  40                  45

Asn Arg Asp Trp Ala Val Glu Tyr Tyr Ala Gln Arg Ala Gln Arg Pro
 50                  55                  60

Gly Thr Leu Ile Ile Thr Glu Gly Thr Phe Pro Ser Pro Gln Ser Gly
 65                  70                  75                  80

Gly Tyr Asp Asn Ala Pro Gly Ile Trp Ser Glu Gln Ile Lys Glu
                 85                  90                  95

Trp Thr Lys Ile Phe Lys Ala Ile His Glu Asn Lys Ser Phe Ala Trp
             100                 105                 110

Val Gln Leu Trp Val Leu Gly Trp Ala Ala Phe Pro Asp Thr Leu Ala
         115                 120                 125

Arg Asp Gly Leu Arg Tyr Asp Ser Ala Ser Asp Asn Val Tyr Met Asn
130                 135                 140

Ala Glu Gln Glu Glu Lys Ala Lys Lys Ala Asn Asn Pro Gln His Ser
145                 150                 155                 160

Ile Thr Lys Asp Glu Ile Lys Gln Tyr Val Lys Glu Tyr Val Gln Ala
                165                 170                 175

Ala Lys Asn Ser Ile Ala Ala Gly Ala Asp Gly Val Glu Ile His Ser
            180                 185                 190

Ala Asn Gly Tyr Leu Leu Asn Gln Phe Leu Asp Pro His Ser Asn Asn
        195                 200                 205

Arg Thr Asp Glu Tyr Gly Gly Ser Ile Glu Asn Arg Ala Arg Phe Thr
    210                 215                 220

Leu Glu Val Val Asp Ala Val Val Asp Ala Ile Gly Pro Glu Lys Val
225                 230                 235                 240

Gly Leu Arg Leu Ser Pro Tyr Gly Val Phe Asn Ser Met Ser Gly Gly
                245                 250                 255

Ala Glu Thr Gly Ile Val Ala Gln Tyr Ala Tyr Val Leu Gly Glu Leu
            260                 265                 270

Glu Arg Arg Ala Lys Ala Gly Lys Arg Leu Ala Phe Val His Leu Val
        275                 280                 285

Glu Pro Arg Val Thr Asn Pro Phe Leu Thr Glu Gly Glu Gly Glu Tyr
    290                 295                 300

Asn Gly Gly Ser Asn Lys Phe Ala Tyr Ser Ile Trp Lys Gly Pro Ile
305                 310                 315                 320

Ile Arg Ala Gly Asn Phe Ala Leu His Pro Glu Val Val Arg Glu Glu
                325                 330                 335

Val Lys Asp Pro Arg Thr Leu Ile Gly Tyr Gly Arg Phe Phe Ile Ser
            340                 345                 350

Asn Pro Asp Leu Val Asp Arg Leu Glu Lys Gly Leu Pro Leu Asn Lys
        355                 360                 365

Tyr Asp Arg Asp Thr Phe Tyr Lys Met Ser Ala Glu Gly Tyr Ile Asp
    370                 375                 380

Tyr Pro Thr Tyr Glu Glu Ala Leu Lys Leu Gly Trp Asp Lys Asn
385                 390                 395

<210> SEQ ID NO 3
<211> LENGTH: 338
<212> TYPE: PRT
<213> ORGANISM: Bacillus subtilis

<400> SEQUENCE: 3

Met Ala Arg Lys Leu Phe Thr Pro Ile Thr Ile Lys Asp Met Thr Leu
1               5                   10                  15

Lys Asn Arg Ile Val Met Ser Pro Met Cys Met Tyr Ser Ser His Glu
            20                  25                  30

Lys Asp Gly Lys Leu Thr Pro Phe His Met Ala His Tyr Ile Ser Arg
        35                  40                  45

Ala Ile Gly Gln Val Gly Leu Ile Ile Val Glu Ala Ser Ala Val Asn
    50                  55                  60

Pro Gln Gly Arg Ile Thr Asp Gln Asp Leu Gly Ile Trp Ser Asp Glu
65                  70                  75                  80

His Ile Glu Gly Phe Ala Lys Leu Thr Glu Gln Val Lys Glu Gln Gly
                85                  90                  95

Ser Lys Ile Gly Ile Gln Leu Ala His Ala Gly Arg Lys Ala Glu Leu
            100                 105                 110

Glu Gly Asp Ile Phe Ala Pro Ser Ala Ile Ala Phe Asp Glu Gln Ser
        115                 120                 125

Ala Thr Pro Val Glu Met Ser Ala Glu Lys Val Lys Glu Thr Val Gln
    130                 135                 140

Glu Phe Lys Gln Ala Ala Arg Ala Lys Glu Ala Gly Phe Asp Val
145                 150                 155                 160

Ile Glu Ile His Ala Ala His Gly Tyr Leu Ile His Glu Phe Leu Ser
                165                 170                 175

Pro Leu Ser Asn His Arg Thr Asp Glu Tyr Gly Gly Ser Pro Glu Asn
            180                 185                 190

Arg Tyr Arg Phe Leu Arg Glu Ile Ile Asp Glu Val Lys Gln Val Trp
        195                 200                 205

Asp Gly Pro Leu Phe Val Arg Val Ser Ala Ser Asp Tyr Thr Asp Lys
210                 215                 220

Gly Leu Asp Ile Ala Asp His Ile Gly Phe Ala Lys Trp Met Lys Glu
225                 230                 235                 240

Gln Gly Val Asp Leu Ile Asp Cys Ser Ser Gly Ala Leu Val His Ala
                245                 250                 255

Asp Ile Asn Val Phe Pro Gly Tyr Gln Val Ser Phe Ala Glu Lys Ile
            260                 265                 270

Arg Glu Gln Ala Asp Met Ala Thr Gly Ala Val Gly Met Ile Thr Asp
        275                 280                 285

Gly Ser Met Ala Glu Glu Ile Leu Gln Asn Gly Arg Ala Asp Leu Ile
    290                 295                 300

Phe Ile Gly Arg Glu Leu Leu Arg Asp Pro Phe Phe Ala Arg Thr Ala
305                 310                 315                 320

Ala Lys Gln Leu Asn Thr Glu Ile Pro Ala Pro Val Gln Tyr Glu Arg
                325                 330                 335

Gly Trp

<210> SEQ ID NO 4
<211> LENGTH: 408
<212> TYPE: PRT
<213> ORGANISM: Artificial Sequence
<220> FEATURE:
<223> OTHER INFORMATION: Estrogen binding protein

<400> SEQUENCE: 4

Met Thr Ile Glu Ser Thr Asn Ser Phe Val Val Pro Ser Asp Thr Lys
1               5                   10                  15

Leu Ile Asp Val Thr Pro Leu Gly Ser Thr Lys Leu Phe Gln Pro Ile
            20                  25                  30

```
Lys Val Gly Asn Asn Val Leu Pro Gln Arg Ile Ala Tyr Val Pro Thr
            35                  40                  45

Thr Arg Phe Arg Ala Ser Lys Asp His Ile Pro Ser Asp Leu Gln Leu
 50                  55                  60

Asn Tyr Tyr Asn Ala Arg Ser Gln Tyr Pro Gly Thr Leu Ile Ile Thr
 65                  70                  75                  80

Glu Ala Thr Phe Ala Ser Glu Arg Gly Ile Asp Leu His Val Pro
                     85                  90                  95

Gly Ile Tyr Asn Asp Ala Gln Ala Lys Ser Trp Lys Lys Ile Asn Glu
                    100                 105                 110

Ala Ile His Gly Asn Gly Ser Phe Ser Ser Val Gln Leu Trp Tyr Leu
             115                 120                 125

Gly Arg Val Ala Asn Ala Lys Asp Leu Lys Asp Ser Gly Leu Pro Leu
        130                 135                 140

Ile Ala Pro Ser Ala Val Tyr Trp Asp Glu Asn Ser Glu Lys Leu Ala
145                 150                 155                 160

Lys Glu Ala Gly Asn Glu Leu Arg Ala Leu Thr Glu Glu Glu Ile Asp
                    165                 170                 175

His Ile Val Glu Val Glu Tyr Pro Asn Ala Ala Lys His Ala Leu Glu
             180                 185                 190

Ala Gly Phe Asp Tyr Val Glu Ile His Gly Ala His Gly Tyr Leu Leu
        195                 200                 205

Asp Gln Phe Leu Asn Leu Ala Ser Asn Lys Arg Thr Asp Lys Tyr Gly
210                 215                 220

Cys Gly Ser Ile Glu Asn Arg Ala Arg Leu Leu Leu Arg Val Val Asp
225                 230                 235                 240

Lys Leu Ile Glu Val Val Gly Ala Asn Arg Leu Ala Leu Arg Leu Ser
                    245                 250                 255

Pro Trp Ala Ser Phe Gln Gly Met Glu Ile Glu Gly Glu Glu Ile His
             260                 265                 270

Ser Tyr Ile Leu Gln Gln Leu Gln Gln Arg Ala Asp Asn Gly Gln Gln
        275                 280                 285

Leu Ala Tyr Ile Ser Leu Val Glu Pro Arg Val Thr Gly Ile Tyr Asp
290                 295                 300

Val Ser Leu Lys Asp Gln Gln Gly Arg Ser Asn Glu Phe Ala Tyr Lys
305                 310                 315                 320

Ile Trp Lys Gly Asn Phe Ile Arg Ala Gly Asn Tyr Thr Tyr Asp Ala
                    325                 330                 335

Trp Pro Glu Phe Lys Thr Leu Ile Asn Asp Leu Lys Asn Asp Arg Ser
             340                 345                 350

Ile Ile Gly Phe Ser Arg Phe Phe Thr Ser Asn Pro Asp Leu Val Glu
        355                 360                 365

Lys Leu Lys Leu Gly Lys Pro Leu Asn Tyr Tyr Asn Arg Glu Glu Phe
370                 375                 380

Tyr Lys Tyr Tyr Asn Tyr Gly Tyr Asn Ser Tyr Asp Glu Ser Glu Lys
385                 390                 395                 400

Gln Val Ile Gly Lys Pro Leu Ala
                    405
```